United States Patent

Fan et al.

Patent Number: 5,509,899
Date of Patent: Apr. 23, 1996

[54] MEDICAL DEVICE WITH LUBRICAIOUS COATING

[75] Inventors: You-Ling Fan, East Brunswick; Lawrence Marlin, Bridgewater, both of N.J.; Ronald A. Sahatjian, Lexington; Steven A. Schultz, Northboro, both of Mass.

[73] Assignee: Boston Scientific Corp., Natick, Mass.

[21] Appl. No.: 310,730

[22] Filed: Sep. 22, 1994

[51] Int. Cl.$^6$ .................................................. A61M 29/00
[52] U.S. Cl. .............................. 604/96; 604/265; 606/194
[58] Field of Search ....................... 604/96–103; 606/191, 606/192, 194, 195, 264–265

[56] References Cited

U.S. PATENT DOCUMENTS 5,061,424 10/1991 Karimi et al. .
5,066,298 11/1991 Hess .
5,229,211 7/1993 Murayama et al. .
5,290,306 3/1994 Trotta et al. .

*Primary Examiner*—C. Fred Rosenbaum
*Assistant Examiner*—Perry E. Van Over

[57] ABSTRACT

A medical balloon and catheter in which the balloon (14) is wrapped and folded upon itself tortuously and tightly so outer surfaces (12) contact each other for insertion into the body and in which the balloon is free of bridging and adhesion between abutting surfaces. The balloon has a base of a continuous polymeric surface (10) expandable from a folded, wrapped configuration with surfaces touching each other into a balloon when inflated. A lubricious, biocompatible, hydrogel coating (11) is disposed on the polymeric surface and a thin, lubricious, blood-compatible coating (12) is disposed upon the hydrogel coating and adheres to it to prevent abutting surfaces of the folded polymeric surfaces from adhering to each other during inflation and to prevent delamination of the hydrogel coating and/or rupture of the balloon. Preferably the blood-compatible coating (12) is polyethylene glycol, methoxy polyethylene glycol or mixtures thereof having a molecular weight between about 100 and 20,000 grams per gram mole.

25 Claims, 1 Drawing Sheet

MEDICAL DEVICE WITH LUBRICAIOUS COATING

BACKGROUND OF THE INVENTION

1. Field of the Invention

The present invention relates to coated substrates for medical purposes. The invention is particularly directed to medical devices or other substrates having lubricious coatings that are stored together where they can touch each other or are tortuously wrapped and folded upon themselves prior to use and are unfolded during use. In particular, one aspect of the present invention relates to lubriciously coated balloons that are folded and wrapped upon themselves for storage and are unwrapped and expanded to a size that is considerably greater than the stored size by the introduction of an expansion fluid into the balloon without having portions stick to each other and possibly removing the lubricious coating or tearing the substrate.

2. Description of the Prior Art

Medical balloon catheters are used surgically for insertion into blood vessels, urethra, or body conduits. Conventionally, such catheters are made of materials such as Nylon, Selar®, polyethylene terephthalate (PET), polyethylene (PE) or similar materials. Also, such balloon catheters can be made of several layers with polyethylene terephthalate blended with polyethylene. Also they can be made with blends of polyethylene terephthalate and Hytrel. Hytrel is a randomized block co-polymer of polyethers and polyesters. Catheters have been rendered lubricious by coating them with a layer of silicone, glycerine or olive oil. Such coatings are not necessarily satisfactory in all cases because they tend to run off and lose the initial lubricity rather rapidly and they can also lack abrasion resistance. Hydrophilic coatings have also been disclosed such as polyvinyl pyrrolidone with polyurethane interpolymers or hydrophilic polymer blends of thermoplastic polyurethane and polyvinyl pyrrolidone.

SUMMARY OF THE INVENTION

Accordingly, the present invention provides a biocompatible surface for a device which can impede blocking or sticking of two polymer surfaces when the surfaces are placed in tight intimate contact with each other such as is the case when the balloon is wrapped for storage or when a surface of one device will contact a surface of another device. Especially, the present invention can be applied to balloon angioplasty catheters and other polymeric devices used for insertion into the body of a mammal which have to be folded and provide contact between the surfaces.

According to one aspect of the present invention, we utilize a continuous polymeric surface that is expandable from a folded, wrapped configuration with the surfaces touching each other into a balloon when inflated. While such polymeric surfaces provide excellent balloon stock they are not necessarily sufficiently lubricious to be used by themselves because the material can be somewhat lacking in lubriciousness. As is conventional, lubricious, biocompatible, hydrophilic coatings called hydrogels are disposed on the polymeric surface. After sterilization or storage, such coatings can become delaminated from the polymeric surface upon expansion of the balloon because they stick to each other, that is they cross polymerize or bridge. The bridging, in some cases, can be so severe that the polymeric surface itself can be ruptured upon inflation.

According to another aspect of the present invention, we utilize other medical devices suitable for insertion into the body of a mammal, e.g., catheters and guidewires. Often, such medical devices are coated with hydrogels in a bundled state and may also be stored or packaged in a bundled state. As a result, hydrogel surfaces from adjacent devices can contact each other and bridge. Thus, the present invention is also directed to inhibiting a first polymeric surface and a second polymeric surface from adhering to each other by applying the anti-blocking agents of the present invention to the surfaces. Typically, the first polymeric surface and the second polymeric surface are comprised of the same material, e.g., a polyolefin. Preferably, both the first polymeric surface and the second polymeric surface comprise a first coating, e.g., a lubricious biocompatible, hydrophilic polymer, disposed thereon and a second coating comprising the anti-blocking agents of the present invention.

According to the invention we provide a thin, lubricious, biocompatible, blood-compatible coating or complex upon the hydrogel coating as an anti-blocking agent. The coating prevents abutting surfaces from adhering to each other, e.g., during inflation of a balloon, and prevents delamination of the hydrophilic coating from the polymeric surface. In particular, we have found that certain polyalkylene glycols and alkoxypolyethylene glycols can provide a thin, lubricious, biocompatible coating that is necessary to prevent the bridging of such surfaces. The polyalkylene glycols and alkoxypolyethylene glycols suitable for use in accordance with the present invention have a molecular weight of about 100 to 30,000 grams per gram mole, preferably from about 100 to 20,000 grams per gram mole and more preferably from about 500 to 10,000 grams per gram mole. At molecular weights greater than about 500 grams per gram mole, the glycols have a desirable waxy consistency. As used herein, the term "molecular weight" means number average molecular weight. Methods for determining number average molecular weight are known to those skilled in the art.

Preferably, the polyalkylene glycols and alkoxy polyalkylene glycols are water soluble. As used herein, the term "water soluble" means that at least 1 weight percent of the polyglycol is soluble in water.

Preferably, the alkylene portion of the polyglycol comprises from about 2 to 4 and more preferably from about 2 to 3 carbon atoms per repeat unit. Preferably, the alkoxy portion of the polyglycol comprises alkyl groups having from 1 to 6 carbon atoms per molecule. The polyglycols can be homopolymers, e.g., polyethylene glycol, or copolymers, e.g., a copolymer of ethylene glycol and propylene glycol. Preferred polyalkylene glycols and alkoxypolyethylene glycols have the formula:

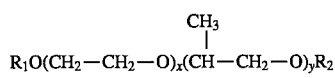

$$R_1O(CH_2-CH_2-O)_x(CH-CH_2-O)_yR_2$$

with $CH_3$ on the CH group.

wherein:
(a) R1 and R2 can be the same or different and can be H or an alkyl group having 1 to about 6 carbon atoms;
(b) x is from 2 to about 500; and
(c) y is from 0 to about 100.

The polyalkylene glycols and alkoxy polyalkylene glycols may also contain functional groups such as, for example, hydroxyl, sulfur, nitrogen or oxygen. Polyethylene glycol and methoxy polyethylene glycol are particularly preferred for use in accordance with the present invention. Preferably, the coating has a thickness effective to inhibit the surfaces from adhering to each other. The coating typically has a thickness greater than about 1 micrometer, also referred to as micron ("µm") and preferably has a thickness between about 1 and 10 µm. While the coating can be used with many polymeric surfaces we have found the coating is especially useful with hydrogel-coated polyethylene terephthalate (PET) and co-extrusions and blends of polymers of PET, polyethylene (PE) and Nylon-based materials.

Lubricious, hydrophilic coatings for medical devices, e.g., catheters, can, for example, comprise a hydrogel mixture of polyethylene glycol and a polymeric hydrophilic material. Polymers have been used which are generally chain-structured, non-crosslinked and water soluble having a hydrophilic group such as —OH, —CONH$_2$, —COOH, —NH$_2$, —COO—, —SO$_3$, and —NR$_3^+$, where R is alkyl or hydrogen have been used. Also useful are natural water-soluble polymers such as carboxymethyl cellulose (CMC), methyl cellulose (MC), hydroxyethyl cellulose (HEC), and hydroxypropyl cellulose (HPC). Synthetic water-soluble polymers, polyethylene oxide, polyethylene glycol, and methoxypolyethylene glycol can be used along with maleic anhydride polymers, e.g., methyl vinyl ether-maleic anhydride copolymers. Moreover, also used are water-soluble Nylons and pyrrolidones, e.g., polyvinyl pyrrolidone. The derivatives of these polymers are not limited to water-soluble ones but may be of any form so long as they have, as a basic structure, the water-soluble polymer as mentioned above. Insolubilized derivatives can also be employed so long as they have freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reaction of the above-mentioned water-soluble polymers. Also useful are polymers crosslinked with substances having more than one reactive functional-group such as diazonium group, azide group, isocyanate group, acid chloride group, acid anhydride group, imino carbonate group, amino group, carboxyl group, epoxy group, hydroxyl group, and aldehyde group. Moreover copolymers with vinyl compounds, acrylic acid, methacrylic acid, diene compounds and maleic anhydride can be used.

According to the aspect of the present invention directed to coatings for medical balloons, we have found that coatings of the above-mentioned polyalkylene glycols and alkoxypolyalkylene glycols and mixtures thereof when applied after drying of the hydrogel coating and before folding of the balloon will prevent blocking of the folded layers of the balloon when it is expanded and will not impede the lubriciousness of the hydrogel.

DESCRIPTION OF THE PREFERRED EMBODIMENTS

Figure 1:
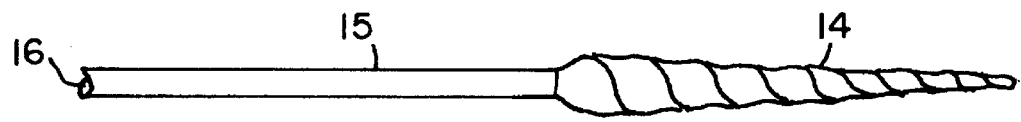
FIG. 1 is a side view of a catheter with a balloon tightly wrapped and folded for insertion for a medical procedure.
Figure 2:
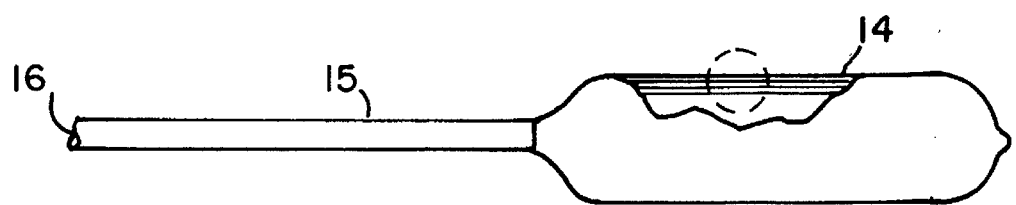
FIG. 2 is a side elevational view, partially cut away to show the coatings of the present invention.
Figure 3:
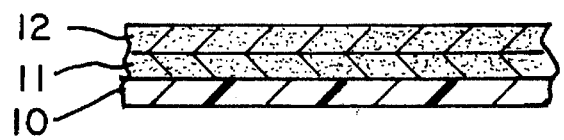
FIG. 3 is an enlarged cross-sectional view taken at the circle in FIG. 2 and showing the coatings.

Referring to the drawings, a hydrogel coating 11 is disposed on a polymeric substrate 10. The substrate 10 forms a balloon 14 that is conventionally connected to a shaft 15 with an internal lumen 16. As seen in FIG. 1, the balloon 14 is folded and wrapped upon itself to reduce the diameter to enable it to be easily introduced into a body part. When inflation fluids are introduced into lumen 16, the balloon 14 will expand to a generally cylindrical shape. A layer of biocompatible, anti-blocking agent 12 is disposed on a layer of hydrogel coating 11. The anti-blocking agent layer 12 has a thickness between 1 and 10 µm.

The hydrogel coating 11 has a thickness between about 1 and 10 µm. The hydrogel coating 11 is a lubricious, hydrophilic material. Water-soluble polymers can be used which are generally chain-structured, non-crosslinked polymers having a hydrophilic group such as —OH, —CONH$_2$, —COOH, —NH$_2$, —COO—, —SO$_3$, and —NR$_3^+$, where R is alkyl or hydrogen. Also used are natural water-soluble polymers such as carboxymethyl cellulose (CMC), methyl cellulose (MC), hydroxyethyl cellulose (HEC), and hydroxypropyl cellulose (HPC). Synthetic water-soluble polymers polyethylene oxide, polyethylene glycol, and methoxypolyethylene glycol are also used. Maleic anhydride polymers, e.g., methyl vinyl ether-maleic anhydride copolymers, were also used. Moreover, also used are water-soluble Nylons and pyrrolidones, e.g., polyvinyl pyrrolidone. The derivatives of these polymers are not limited to water-soluble ones but may be of any form so long as they have, as a basic structure, the water-soluble polymer as mentioned above. Insolubilized derivatives are also employed so long as they have freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reaction of the above-mentioned water-soluble polymers. Also used are polymers crosslinked with substances having more than one reactive functional-group such as diazonium group, azide group, isocyanate group, acid chloride group, acid anhydride group, imino carbonate group, amino group, carboxyl group, epoxy group, hydroxyl group, and aldehyde group. Moreover copolymers with vinyl compounds, acrylic acid, methacrylic acid, diene compounds, and maleic anhydride have been used. Water soluble cellulosic polymers such as carboxymethyl cellulose, methyl cellulose, hydroxyethyl cellulose and hydroxypropyl cellulose, maleic anhydride polymers (e.g., methyl vinyl ether-maleic anhydride copolymers), water soluble Nylon®, poly(carboxylic acids) or polyurethane are useful. Preferably the hydrogel is polyacrylic acid and is sold under the trade name of Carbopol and made by B. F. Goodrich Corp. of Cleveland, Ohio.

The substrate 10 of the catheter body is primarily manufactured of polyethylene terephthalate (PET). In alternative embodiments the polyethylene terephthalate can be mixed with Selar or Hytrel (in ratios between about 1 and 99 weight percent) and then co-extruded over polyethylene terephthalate as a laminated construction. Other polymeric materials can include polyolefins such as, for example, polypropylene and polyethylene, polyurethane, engineering thermoplastic elastomers, polyamides and liquid crystal polymers.

In a preferred embodiment, the coating mixture to form the hydrogel is prepared by contacting the substrate or medical device, such as a catheter, with a primer coating agent, e.g., polyisocyanate, in a liquid medium, particularly an oligomer or prepolymer of an aliphatic or aromatic diisocyanate to promote bonding of the hydrophilic coating to the device. The formed lubricious, biocompatible, hydrophilic coating can be a dried admixture of polymers of polycarboxylic acid and polyisocyanate wherein the polycarboxylic acid has a molecular weight between about 1,000,000 and 8,000,000 grams per gram mole. The liquid medium can be removed by drying or the catheter can be treated directly with a high molecular weight poly(carboxylic acid) in a liquid medium. After drying in an oven, a non-tacky, easy-to-handle, and uniformly coated catheter is obtained. The mixture is applied to the substrate by conventional coating applying techniques such as dipping, spraying, wiping, painting and the like. The preferred method of applying the hydrogel involves dipping the catheter into the above-mentioned solutions.

After coating the substrate, the catheter is dipped into an aqueous, buffered solution to quench any residual polyisocyanate and the product is then dried for a sufficient length of time to insure removal of any of the carrier solvents.

The dried coating of hydrogel is then treated with the blood-compatible anti-blocking agent of the present invention, as described above, to prevent the wrapped product from sticking.

In a preferred embodiment we use polyethylene glycols or methoxy polyethylene glycols. Polyethylene glycols are sold, for example, under the trade name Carbowax® Polyethylene Glycols (Carbowax is the trade name of the polyethylene glycol family of products manufactured by Union Carbide Corporation, Danbury, Conn.). Polyethylene glycols are a waxy substance at molecular weights greater than about 500 grams per gram mole and higher and a liquid substance at lower molecular weights. Polyethylene glycols are soluble in water or fluids contained in blood and provides a coating for the lubricious hydrogel disposed therebeneath. They can also dissolve from the catheter upon application of water, saline or body fluids. The coating is typically formed in thicknesses greater than 1 μm and preferably between about 1 and 10 μm, by conventional techniques such as described above and then dried.

After the first drying step, the catheter is dipped in an aqueous solution comprising polyethylene glycol or methoxy polyethylene glycol in a pH 7.0 balanced sodium phosphate solution. This step is followed by a second drying step to remove water from the coated substrate.

Hydrophilic coatings on certain substrates have the propensity to adhere to themselves causing either a delamination of the hydrophilic coating from the substrate or tearing of the substrate completely. Many potential remedies have been tried to reduce the occurrence of the blocking of the coating including the addition of compounds to the coating fluids or the addition of compounds on to the coated surface itself. Some of these added compounds include, but are not restricted to, salts, silicones, mineral oil, and the polyglycols.

The coatings described above can often completely eliminate the blocking of the coating without any additional adverse effects. For example, both the silicones and the mineral oil caused the hydrophilic coating to hydrate at a much slower rate and did not adequately solve the blocking problem. Dipping the finished catheter in a solution of isotonic saline solution (0.85% w/w) allowed faster hydration, but did not solve the blocking problem. The polyethylene glycols and alkoxypolyalkylene glycols of the present invention adequately solved the blocking problem while allowing complete and fast hydration of the hydrophilic coating.

The following examples are illustrative of substrates, hydrogels and various coatings on the hydrogels which are useful according to the present invention. Such examples are merely illustrative and are not to be considered to be limitative on the claims.

Balloons were coated with various hydrogels and then they were subsequently coated with an aqueous solution containing polyethylene glycol. As an example, balloons coated with Hydromer (a trademarked product of Hydromer, Inc. of Whitehouse, N.J.), a polyvinyl pyrrolidone hydrophilic coating, were broken into two groups where half underwent the subsequent coating of an aqueous solution containing polyethylene glycol and half were not coated with polyethylene glycol.

Both groups were folded and sterilized prior to testing. Of the eight balloons which were coated with the polyethylene glycol solution, none showed any signs of blocking and in all cases the balloon coatings were very smooth. Of the seven balloons which were not coated with the polyethylene glycol solution, one of the balloons showed a slight amount of blocking or adhesion to itself and several balloons showed signs of increased pressure required to unfold and open the balloons.

EXAMPLE 1

This example illustrates a typical anti-blocking coating composition, as well as the hydrophilic coating composition the anti-blocking coating was applied to, and the process used in this invention. A polyethylene terephthalate angioplasty balloon (attached to a catheter shaft) was wiped clean with Freon® and air dried for five minutes. The angioplasty balloon was then coated with Polyslip™ P-106 polyisocyanate-based primer solution for one minute (Polyslip™ chemicals are manufactured by Union Carbide Corporation of Danbury, Conn.). This was followed by drying in a forced air oven set at 75° C. for 30 minutes. The primer-coated angioplasty balloon was then coated with Polyslip™ T-503M polycarboxylic acid-based top coat solution for one second. This was followed by drying in a forced air oven set at 75° C. for 60 minutes. The coated catheter was then quenched in an aqueous solution of a mixture of phosphate salts of an alkali metal followed by drying in a forced air oven set at 75° C. for 10 hours to stop the reaction of the Polyslip™ P-106 and the Polyslip™ T-503M. Although the balloons had a normal plastic feel when dry, and subsequently became instantly lubricious upon exposure to water or body fluids, it was found that if the balloon were deflated and folded as in FIG. 1 for insertion into a protective cover, as is common to reduce the profile of the product prior to sterilization and use in a medical procedure, that upon inflation the hydrophilic coating stuck to itself and the coating would delaminate from the substrate causing catastrophic failure of the substrate in some instances.

A 4% solution of Carbowax® Polyethylene Glycol 8000, having a molecular weight of about 8000 grams per gram mole, in an aqueous solution of a mixture of phosphate salts of an alkali metal was applied to the hydrophilic-coated balloons after the 10 hour baking step described above. The samples were then dried in a forced-air oven for one hour at 75° C. To reduce the profile of the product prior to sterilization and use in a medical procedure, the balloons were folded as in FIG. 1 for insertion into a protective cover. After sterilization, the balloons were inflated and it was found that the hydrophilic coating did not stick to itself at all. The balloons had a normal plastic feel when dry, and subsequently would become instantly lubricious upon exposure to water or body fluids.

EXAMPLE 2

A polyethylene terephthalate angioplasty balloon was coated with the Polyslip™ hydrophilic coating system described in Example 1 except that Hydromer™ polyvinylpyrrolidone hydrophilic coating is used as the top coat instead of the Polyslip™ T-503M described above. Half of the balloons were then coated in a 4% solution of Carbowax® Polyethylene Glycol 8000 in an aqueous solution of a mixture of phosphate salts of an alkali metal and then subjected to a 1 hour baking step as described above. To reduce the profile of the product prior to sterilization and use in a medical procedure, the balloons were folded as in FIG. 1 for insertion into a protective cover.

After sterilization, the balloons were inflated. All of the samples which received the subsequent treatment in the 4% solution of Carbowax® Polyethylene Glycol 8000 opened without the hydrophilic coating sticking to itself. The balloons had a normal plastic feel when dry, and subsequently would become instantly lubricious upon exposure to water or body fluids. Of the samples which did not receive the subsequent treatment in the 4% solution of Carbowax® Polyethylene Glycol 8000, 15% showed signs of the coating adhering to itself.

It is apparent that modifications and changes can be made within the spirit and scope of the present invention but it is our intention, however, only to be limited by the scope of the appended claims.

As our invention we claim.

1. A medical device for insertion into the body of a mammal, comprising a first polymeric surface which is at least periodically subjected to contacting with a second polymeric surface; said first polymeric surface comprising:
   (A) a first hydrophilic coating disposed on said first polymeric surface; and
   (B) a lubricious, blood-compatible second coating comprising a polyalkylene glycol or alkoxy polyalkylene glycol having a molecular weight of from about 100 to 30,000 grams per gram mole, said blood-compatible coating disposed at least partially upon and adhering to said first coating,
   wherein said second coating is present to inhibit said first surface and said second surface from adhering to each other.

2. The medical device according to claim 1 wherein said first coating is a lubricious, biocompatible, hydrophilic polymer.

3. The medical device according to claim 2 wherein the blood-compatible coating comprises polyethylene glycols, methoxy polyethylene glycols or mixtures thereof having a molecular weight between about 100 and 20,000 grams per gram mole.

4. The medical device according to claim 1 wherein the blood-compatible coating has a thickness greater than about 1 µm.

5. The medical device according to claim 2 wherein the lubricious, biocompatible, hydrophilic polymer comprises at least one polycarboxlyic acid.

6. The medical device according to claim 1 further comprising a primer coating beneath said first coating, said primer coating comprising a polyisocyanate.

7. The medical device according to claim 2 wherein the lubricious, biocompatible, hydrophilic coating is formed of a admixture of polymers of polycarboxylic acid and polyisocyanate.

8. The medical device according to claim 1 wherein the second coating comprises polyethylene glycols, methoxy polyethylene glycols or mixtures thereof having a molecular weight between about 100 and 20,000 grams per gram mole.

9. The medical device according to claim 8 wherein the second coating further comprises a polycarboxylic acid.

10. The medical device according to claim 1 wherein said first polymeric surface comprises at least one polymer selected from the group consisting of polyethylene terephthalate, polypropylene, polyurethane, polyester and Nylon.

11. The medical device according to claim 1 which is a balloon.

12. The medical device according to claim 11 wherein said balloon is folded upon itself for storage and insertion into the body, said first polymeric surface and said second polymeric surface comprising abutting portions of an outer surface of said balloon.

13. The medical device according to claim 12 wherein said balloon has a distal and a proximal end, and further including a shaft having at least one internal lumen disposed therein, said lumen being in fluid flow communication with the proximal end of said balloon whereby to provide for the introduction of inflation fluids.

14. The medical device according to claim 1 which is a catheter.

15. The medical device according to claim 14 wherein said first polymeric surface comprises a portion of an outer surface of said catheter.

16. The medical device according to claim 15 wherein said second polymeric surface comprises a different portion of said outer surface of said catheter.

17. The medical device according to claim 15 wherein said second polymeric surface comprises a portion of an outer surface of a different catheter in contact with said catheter.

18. A medical balloon folded upon itself for storage and insertion into the body, said balloon being substantially free of bridging and adhesion between abutting surfaces, said balloon comprising:
   a continuous polymeric surface expandable from a folded, wrapped configuration with outer surfaces touching each other into a balloon when inflated;
   a lubricious, biocompatible, hydrophilic coating disposed on the outer surfaces of said polymeric surface;
   a thin, lubricious coating of a polyalkylene glycol or alkoxy polyalkylene glycol disposed upon and adhering to said hydrophilic coating to prevent abutting surfaces of said polymeric surface from adhering to each other and delaminating said hydrophilic coating from said polymeric surface during inflation.

19. The balloon according to claim 18 further comprising a catheter shaft having a lumen therein in open communication with said balloon.

20. A medical balloon used for catheters where the balloon is folded for insertion into the body, said balloon being free of bridging and adhesion between abutting surfaces when expanded, said balloon comprising:
   a continuous polymeric surface including polyethylene terephthalate that is expandable from the folded configuration with surfaces touching each other into a generally cylindrically-shaped balloon when inflated;
   a lubricious, biocompatible, hydrophilic coating disposed on outer surfaces of said polymeric surface said coating comprising at least one polymer selected from the group consisting of:
   (A) water soluble polymers of generally chain-structured, non-crosslinked polymers having a hydrophilic group such as —OH, —$CONH_2$, —COOH, —$NH_2$, —COO—, —$SO_3$, and —$NR_3^+$, where R is alkyl or hydrogen,
   (B) natural polymers of cellulose, carboxymethyl cellulose, methyl cellulose, hydroxyethyl cellulose and hydroxypropyl cellulose, (C) synthetic water-soluble polymers of polyethylene oxide, polyethylene glycol and methoxypolyethylene glycol,
(D) methyl vinyl ether-maleic anhydride copolymers,
(E) water-soluble Nylons,
(F) polyvinyl pyrrolidone,
(G) insoluble derivatives of these polymers having as a basic structure, the water-soluble polymer as mentioned above and hydratable insolubilized derivatives of such polymers having freedom in the molecular chain including esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reaction of the above-mentioned water-soluble polymers and polymers crosslinked with substances having more than one reactive functional-group including a diazonium group, azide group, isocyanate group, acid chloride group, acid anhydride group, imino carbonate group, amino group, carboxyl group, epoxy group, hydroxyl group, and aldehyde group and copolymers with vinyl compounds, acrylic acid, methacrylic acid, diene compounds, and maleic anhydride;

a lubricious coating of a polyethylene glycol, methoxy polyethylene glycol, or mixtures thereof, having a molecular weight of from about 100 to 20,000 grams per gram mole, said lubricious coating having a thickness greater than about 1 μm disposed upon and adhering to said hydrophilic coating sufficient to substantially prevent abutting surfaces from the folded balloon from adhering to each other during inflation.

21. The balloon according to claim 20 wherein the polyethylene glycols or methoxy polyethylene glycols have the formula:

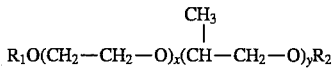

wherein:
(a) R1 and R2 can be the same or different and can be H or an alkyl group having 1 to about 6 carbon atoms;
(b) x is from 2 to about 500; and
(c) y is from 0 to about 100.

22. The balloon according to claim 20 wherein the lubricious, hydrophilic coating is formed of a dried admixture of polymers of polycarboxylic acids and polyisocyanate.

23. The balloon according to claim 22 wherein said polymer of polycarboxylic acid has a molecular weight of about 1,000,000 and 8,000,000 grams per gram mole.

24. The balloon according to claim 20 wherein the balloon is tortuously and tightly wrapped upon itself so outer surfaces contact each other.

25. The balloon according to claim 20 wherein said balloon has a distal and a proximal end, and further including a shaft having at least one internal lumen disposed therein, said lumen being in fluid flow communication with the proximal end of said balloon whereby to provide for the introduction of inflation fluids.

* * * * *